(12) United States Patent
Askill et al.

(10) Patent No.: US 6,214,332 B1
(45) Date of Patent: Apr. 10, 2001

(54) METHODS FOR CLOSING SUTURABLE WOUNDS BY USE OF CYANOACRYLATE ESTER COMPOSITIONS COMPRISING AN ANTIMICROBIAL AGENT

(75) Inventors: Ian N. Askill, Colorado Springs, CO (US); Richard J. Greff, St. Pete Beach, FL (US); Michael M. Byram, Colorado Springs, CO (US)

(73) Assignee: MedLogic Global Corporation, Colorado Springs, CO (US)

( * ) Notice: Subject to any disclaimer, the term of this patent is extended or adjusted under 35 U.S.C. 154(b) by 0 days.

(21) Appl. No.: 09/005,973

(22) Filed: Jan. 12, 1998

Related U.S. Application Data

(63) Continuation-in-part of application No. 08/912,681, filed on Aug. 18, 1997, which is a continuation-in-part of application No. 08/781,409, filed on Jan. 10, 1997, now Pat. No. 5,684,042.

(51) Int. Cl.$^7$ .................................................. A61K 31/765
(52) U.S. Cl. ..................................... 424/78.37; 424/78.06
(58) Field of Search .............................. 424/78.37, 78.06

(56) References Cited

U.S. PATENT DOCUMENTS

| | | |
|---|---|---|
| 2,784,127 | 3/1957 | Joyner et al. . |
| 3,223,083 | 12/1965 | Cobey . |
| 3,524,537 | 8/1970 | Winter . |
| 4,323,557 | 4/1982 | Rosso et al. . |
| 4,374,126 | 2/1983 | Cardarelli et al. . |
| 4,542,012 | 9/1985 | Dell . |
| 4,713,235 | 12/1987 | Krall . |
| 4,978,527 | 12/1990 | Brink et al. . |
| 4,994,542 | 2/1991 | Matsuda et al. . |
| 5,051,256 | 9/1991 | Barnes . |
| 5,069,907 | 12/1991 | Mixon et al. . |
| 5,071,648 | 12/1991 | Rosenblatt . |
| 5,306,490 | 4/1994 | Barley, Jr. . |
| 5,328,687 | 7/1994 | Leung et al. . |
| 5,350,573 | 9/1994 | Goldberg et al. . |
| 5,383,899 | 1/1995 | Hammerslag . |
| 5,480,935 | 1/1996 | Greff et al. . |
| 5,547,662 | 8/1996 | Khan et al. . |
| 5,580,565 | 12/1996 | Tighe et al. . |
| 5,684,042 | * 11/1997 | Greff et al. ........................ 574/527 |

FOREIGN PATENT DOCUMENTS

WO 96/23532   8/1996   (WO) .

OTHER PUBLICATIONS

Ritter, M.A., et al., "Retrospective Evaluation of an iodophor–Incorporated Antimicrobial Plastic Adhesive Wound Drape"—Clinical Orthopedics and Related Research, (1986) pp. 307–308.

Cagle, Charles V. (Editor), "*Handbook of Adhesive Bonding*", (1970), Chapter 29, p. 29–1 "Surgical and Dental Adhesives", Lee, Henry, et al.

Sidorova, et al., *Preventing Incompetence of Uterine Sutures after Ceasarian Section*, Akusherstvo I. Ginekologiia, (Mar. 1989) 3:30–33.

Skeist, I., (Edited by), "*Handbook of Adhesives*", (1970) Chapter 31, pp. 409–413, "Cyanoacrylate Adhesives", Coover, Jr., H.W.

Timokhina, V.I., "*Biological Properties of New Adhesion Compositions of Medical Purpose*", Biodestruktiruysshchve Polim. Mater. (1982) 55–61.

* cited by examiner

*Primary Examiner*—Thurman K. Page
(74) *Attorney, Agent, or Firm*—Burns, Doane, Swecker & Mathis, LLP

(57) ABSTRACT

Antimicrobial cyanoacrylate compositions are applied to suturable wound surfaces to close the wound surface.

17 Claims, No Drawings

METHODS FOR CLOSING SUTURABLE WOUNDS BY USE OF CYANOACRYLATE ESTER COMPOSITIONS COMPRISING AN ANTIMICROBIAL AGENT

CROSS-REFERENCE TO RELATED APPLICATIONS

This application is a continuation-in-part of pending application Ser. No. 08/912,681 filed Aug. 18, 1997 which, in turn is a continuation-in-part of application Ser. No. 08/781,409 filed Jan. 10, 1997, now U.S. Pat. No. 5,684,042, issued Nov. 4, 1997, both of which are incorporated herein by reference in their entirety.

BACKGROUND OF THE INVENTION

1. Field of the Invention

This invention is directed to methods for closing opposed skin sections of suturable wounds by using polymerizable cyanoacrylate compositions comprising a compatible antimicrobial agent and, in particular, an iodine containing antimicrobial agent. These antimicrobial cyanoacrylate compositions provide for in situ formation of an antimicrobial polymeric cyanoacrylate film which film joins the separated skin sections of the suturable wound and, in a preferred embodiment, forms a covering over the closed wound.

2. References

The following publications, patent applications and patents are cited in this application as superscript numbers:

1 Barley, et al., International Patent Application Publication No. WO 93/25196, for Methods for Treating Non-Suturable Wounds by Use of Cyanoacrylate Adhesives, published Dec. 23, 1993
2 Barley, et al., Methods for Treating Suturable Wounds by Use of Sutures and Cyanoacrylate Adhesives, U.S. Pat. No. 5,254,132, issued Oct. 19, 1993
3 Greff, et al., U.S. Pat. No. 5,480,935, Cyanoacrylate Adhesive Compositions, issued Jan. 2, 1996
4 Beller, et al., Process for the Preparation of Iodine-Polyvinylpyrrolidone by Dry Mixing, U.S. Pat. No. 2,706,701, issued Apr. 19, 1955
5 Hosmer, Process of Stabilizing Polyvinylpyrrolidone, U.S. Pat. No. 2,826,532, issued Mar. 11, 1958
6 Siggin, Preparation of Iodine Polyvinylpyrrolidone Adducts, U.S. Pat. No. 2,900,305, issued Aug. 18, 1958
7 Joyner, et al., Plasticized Monomeric Adhesive Compositions and Articles Prepared Therefrom, U.S. Pat. Nos. 2,784,127, issued Mar. 5, 1957
8 Columbus, et al., Adhesive Cyanoacrylate Compositions with Reduced Adhesion to Skin, U.S. Pat. No. 4,444,933, issued Apr. 24, 1984
9 Leung, et al., Biocompatible Monomer and Polymer Compositions, U.S. Pat. No. 5,328,687, issued Jul. 12, 1994
10 Leplyanin, "Medical and Surgical Adhesive Composition and Process for Its Preparation", International Application Publication No. WO 96/23532 published Aug. 8, 1996
11 Greff, et al., Cyanoacrylate Adhesive Compositions, U.S. Pat. No. 5,665,817, issued Sep. 9, 1997
12 Quinn, et al., A Randomized Trial Comparing Octylcyanoacrylate Tissue Adhesive and Sutures in the Management of Lacerations, J. Amer. Med. Assoc., (May 21, 1997) 277(19):1527–1530

All of the above patent applications and patents are herein incorporated by reference in their entirety to the same extent as if each individual publication, patent application or patent was specifically and individually indicated to be incorporated by reference in its entirety.

STATE OF THE ART

Polymerizable cyanoacrylate esters have been disclosed for a variety of topical uses on mammalian skin including use in covering small non-suturable superficial wounds on skin surfaces[1] as well as in closing suturable wounds.[2] Polymerizable cyanoacrylate esters suggested for such uses include cyanoacrylate esters of formula I:

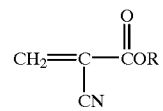

wherein R is an alkyl or other suitable substituent. Such cyanoacrylate esters are disclosed in U.S. Pat. Nos. 3,527,224; 3,591,676; 3,667,472; 3,995,641; 4,035,334; and 4,650,826. Preferably, when applied to mammalian tissue, R is an alkyl group of from 1 to 10 carbon atoms and most often is butyl or octyl (e.g., n-butyl or n-octyl).

These compositions are liquid in nature and, upon contact with surface skin proteins and moisture, will polymerize and the resulting polymer bonds strongly to the skin. When a cyanoacrylate ester is applied over apposed skin sections of a suturable wound, subsequent polymerization will result in joining these apposed skin sections, and, hence, closure of the wound.

Cyanoacrylate ester compositions used for closing suturable wounds typically are formulated to contain a polymerization inhibitor to avoid premature polymerization of the formulation. Notwithstanding the benefits associated with the use of polymerizable cyanoacrylate ester compositions for application with suturable wounds, these compositions do not have a broad spectrum of antimicrobial activity including activity against microbial spores and, accordingly, cannot guarantee reductions in microbial populations on mammalian skin surface either under or adjacent the closed wound. Infection at the site of suturable wounds closed by conventional methods is, however, a significant health care concern. Accordingly, the use of polymerizable cyanoacrylate ester compositions for closing suturable wounds would be significantly augmented if these compositions were also widely antimicrobial.

Because polymerizable cyanoacrylate ester compositions alone are not sufficiently antimicrobial, incorporation of broad antimicrobial properties into the cyanoacrylate polymeric film necessitates, of course, that an antimicrobially effective amount of an antimicrobial agent be incorporated into the polymerizable cyanoacrylate ester composition and that sufficient amounts of this agent be released from the resulting polymeric cyanoacrylate film formed in situ on the patient's skin such that an antimicrobial effect is achieved. The incorporation of such an antimicrobial agent into the cyanoacrylate ester composition is problematic at best because several disparate criteria must be simultaneously met. First, the antimicrobial agent must be soluble or dispersible in the cyanoacrylate ester composition at the concentrations necessary to effect antimicrobial properties. Second, the antimicrobial agent employed must not cause premature polymerization of the cyanoacrylate ester composition. Third, the antimicrobial agent employed must not prevent in situ polymerization of the cyanoacrylate ester composition when applied to the skin. Fourth, the antimicrobial agent must be compatible with the intended use of the polymeric film by not inhibiting formation of a durable film. Finally, the impregnated antimicrobial agent must be released from the polymerized film in situ on the patient's skin in sufficient amounts to be antimicrobial.

Because of these disparate properties, many conventional antimicrobial agents are unsuitable for use in the polymerizable cyanoacrylate ester compositions used in the methods of this invention. However, in view of the clear benefits associated with the incorporation of an antimicrobial agent directly into these compositions, methods for closing suturable wounds using antimicrobial cyanoacrylate ester compositions would be particularly beneficial.

SUMMARY OF THE INVENTION

This invention is drawn to methods for closing opposed skin sections of suturable wounds by joining opposed skin sections together, applying an antimicrobial polymerizable cyanoacrylate ester composition to at least one surface of the opposed skin sections and subsequently polymerizing the cyanoacrylate ester in situ. In one embodiment, the opposed skin sections are brought together prior to application of the cyanoacrylate composition which is then applied over the closed sections. In another embodiment, the opposed skin sections are brought together after application of the cyanoacrylate to at least one surface of the opposed skin sections.

In particular, this invention is directed to methods for closing opposed skin sections of suturable wounds which methods utilize cyanoacrylate ester compositions comprising an antimicrobially effective amount of a compatible iodine containing antimicrobial agent. These compositions provide for in situ formation of an antimicrobial polymeric cyanoacrylate film which joins the opposed skin sections together. The specific antimicrobial agent employed is compatible with the cyanoacrylate ester composition insofar as the antimicrobial agent neither causes premature polymerization nor prevents polymerization of the monomer or reactive oligomer, rather a flexible and durable polymer film is formed in situ on mammalian skin by this composition. Moreover, in vitro assays evidence that the antimicrobial agent is released from the polymeric film in antimicrobially effective amounts thereby imparting antimicrobial properties to the polymeric film formed in situ.

The compatible iodine containing antimicrobial agent comprises an antimicrobial complex of iodine molecules with a biocompatible polymer. Suitable biocompatible polymers include, by way of example only, polyvinylpyrrolidinone polymer, which is also referred to under the common name of Povidone or PVP. PVP polymers form complexes with iodine which are antimicrobial in nature and are available commercially as Povidone-Iodine or PVP-I.

This invention is based, in part, on the discovery that application of an antimicrobial polymerizable cyanoacrylate ester composition to at least one of the opposed skin sections of a suturable wound provides for an antimicrobial polymeric film which joins the opposed skin sections. In a preferred embodiment, after closing the wound, a polymeric film or coating is then formed over the closed wound which film not only protects the suturable wound from abrasions, etc. but also reduces the likelihood of infection in the wound.

Accordingly, in one of its method aspects, this invention is directed to a method for closing suturable wounds in a mammalian patient which method comprises:

applying to at least one of the separated skin sections defining the suturable wound a sufficient amount of an antimicrobial polymerizable cyanoacrylate ester composition so as to cover the skin surface;

bringing the separated skin sections defining the suturable wound into apposition; and polymerizing the antimicrobial cyanoacrylate ester composition so as to join the separated skin sections together, wherein the antimicrobial cyanoacrylate ester composition comprises:
(a) a polymerizable cyanoacrylate ester; and
(b) an antimicrobially effective amount of a complex of iodine molecules with a biocompatible polymer.

In another of its method aspects, this invention is directed to a method for closing suturable wounds in a mammalian patient which method comprises:

bringing the separated skin sections defining the suturable wound into apposition;

applying to the skin sections defining the suturable wound a sufficient amount of an antimicrobial polymerizable cyanoacrylate ester composition so as to cover the wound; and polymerizing the antimicrobial cyanoacrylate ester composition so as to join the separated skin sections together, wherein the antimicrobial cyanoacrylate ester composition comprises:
(a) a polymerizable cyanoacrylate ester; and
(b) an antimicrobially effective amount of a complex of iodine molecules with a biocompatible polymer.

Preferably, the polymerizable cyanoacrylate ester is a polymerizable monomer, reactive oligomer or a mixture of monomers and/or oligomers of a cyanoacrylate ester which, in monomeric form, is represented by formula I:

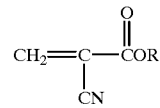

wherein R is selected from the group consisting of:
alkyl of 1 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

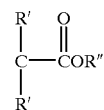

wherein each R' is independently selected from the group consisting of:
hydrogen and methyl, and R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms, aralkyl selected from the group consisting of benzyl, methylbenzyl and phenylethyl, phenyl, and phenyl substituted with 1 to 3 substituents selected from the group consisting of hydroxy, chloro, bromo, nitro, alkyl of 1 to 4 carbon atoms, and alkoxy of from 1 to 4 carbon atoms.

More preferably, in the cyanoacrylate esters of formula I, R is alkyl of from 2 to 10 carbon atoms and still more preferably alkyl of from 4 to 10 carbon atoms. Even more preferably, R is butyl, octyl, decyl or mixtures thereof. Most preferably, R is n-butyl so that the cyanoacrylate ester in monomeric form, is represented by formula II:

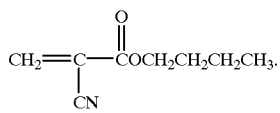

II

Preferred complexes of iodine molecules with a biocompatible polymer include povidone-iodine (commercially available from BASF, Mt. Olive, N.J., USA).

DETAILED DESCRIPTION OF THE PREFERRED EMBODIMENTS

This invention is directed to methods for closing suturable wounds with polymerizable cyanoacrylate ester compositions comprising an antimicrobially effective amount of a compatible iodine containing antimicrobial agent. However, prior to discussing this invention in further detail, the following terms will first be defined.

Definitions

As used herein, the following terms have the following meanings:

The term "suturable wounds" means wounds which are typically closed with sutures or staples whether used alone or in combination with cyanoacrylate adhesives. Such wounds generally are characterized by a first and second separated skin section which are opposed to each other such as those skin wounds formed by a scalpel. Closure of these wounds requires that the separated skin sections are brought into apposition prior to closure.

Typically, suturable wounds are of sufficient severity that non-suturable techniques to close the wound are not applicable nor advised. In most instances, suturable wounds occur either as part of a surgical procedure or as a result of physical trauma to the patient. Additionally, a "steri strip" closure is sometimes performed when the wound is small and simple, such as a one inch laparoscopic incision.

The term "polymerizable cyanoacrylate esters compositions" refers to polymerizable compositions comprising cyanoacrylate ester monomers and/or polymerizable oligomers which, in their monomeric form, are preferably compounds represented by formula I as described above.

More preferably, in formula I, R is an alkyl group of from 1 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl, octyl, decyl or mixtures thereof and most preferably, R is n-butyl. Mixtures of such compounds can also be employed. These polymerizable cyanoacrylate esters are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

The polymerizable cyanoacrylate esters described herein rapidly polymerize in the presence of water vapor or tissue protein, and the n-butyl-cyanoacrylate bonds human skin tissue without causing histotoxicity or cytotoxicity.

The term "a biocompatible polymer" refers to polymers which, as iodine complexes (adducts), are compatible with in vivo applications of cyanoacrylate ester compositions onto mammalian skin including human skin. Representative polymers include polyvinylpyrrolidone, copolymers comprising polyvinylpyrrolidone which is optionally crosslinked, and the like. Suitable copolymers include copolymers of polyvinylpyrrolidone and vinyl acetate or other vinyl compounds which copolymers are optionally crosslinked with a polyisocyanate. The molecular weight of these polymers is not critical with number average molecular weights ranging from about 10,000 to about 1,000,000 and preferably from 30,000 to 300,000 being preferred.

The term "a complex of iodine molecules with a biocompatible polymer" refers to an antimicrobial complex formed by the addition of iodine ($I_2$) to the biocompatible polymer. Such complexes are well known in the art and the resulting complex typically comprises both available iodine and iodine anions. These complexes, on contact with mammalian skin, are antimicrobial apparently by providing for a source of antimicrobial iodine. In any event, such complexes are employed only as starting materials herein and, by themselves, do not form a part of this invention.

These complexes are sometimes referred to herein simply by the term "iodine/polymer complexes". Such iodine/polymer complexes are distinguished from antibiotics which are frequently naturally derived materials from either bacteria or fungi and whose mode of action is to interfere with bacterial processes resulting in bacterial death. Contrarily, the complexes used in this invention are indiscriminate in destroying any microbes including fungi, viruses and bacteria apparently by release of iodine into the microbes and, accordingly, are properly referred to as antimicrobial agents. Surprising, it has been found that of the antimicrobial agents tested, only the iodine/polymer complexes are compatible in cyanoacrylate ester compositions. In fact, elemental (solid) iodine is incompatible with cyanoacrylate ester compositions because the addition of elemental iodine renders such compositions non-polymerizable on mammalian skin. Accordingly, complexation of the iodine with the biocompatible polymer is apparently essential for compatibility with the cyanoacrylate ester composition.

A preferred iodine/polymer complex for use in the compositions of this invention is a polyvinylpyrrolidone iodine complex which is described in, for example, U.S. Pat. Nos. 2,706,701, 2,826,532 and 2,900,305[4,5,6] as well as at pp. 1220 of the Eleventh Edition of the Merck Index, Published by Merck & Co., Rahway, N.J., USA (1989) the disclosures of which are incorporated herein by reference in their entirety. This complex is commercially available under the name "povidone-iodine" from BASF, Mt. Olive, N.J., USA.

The term "biocompatible plasticizer" refers to any material which is soluble or dispersible in the cyanoacrylate ester composition, which increases the flexibility of the resulting polymer film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127[7] and 4,444,933[8] the disclosures of both of which are incorporated herein by reference in their entirety. Specific plasticizers include, by way of example only, acetyl tri-n-butyl citrate (preferably ~20 weight percent or less), acetyl trihexyl citrate (preferably ~20 weight percent or less) butyl benzyl phthalate, dibutyl phthalate, dioctylphthalate, n-butyryl tri-n-hexyl citrate, diethylene glycol dibenzoate (preferably ~20 weight percent or less) and the like. The particular biocompatible plasticizer employed is not critical and preferred plasticizers include dioctylphthalate and acetyl tri-n-butyl citrate.

The term "polymerization inhibitor" refers to conventional inhibitors of cyanoacrylate esters including materials such as sulfur dioxide, glacial acetic acid, and the like. The polymerization inhibitor is typically employed in amounts effective to inhibit polymerization until application onto the mammalian skin. Because of its compatibility with topical skin applications, the polymerization inhibitor is preferably sulfur dioxide which is preferably employed at from about 50 to 500 ppm, preferably 200 to 500 ppm, based on the total weight of the composition. Other preferred polymerization inhibitors include glacial acetic acid, free radical inhibitors (e.g., hydroquinones, 4-methoxyphenol) and the like which can be used alone or in combination with $SO_2$.

The term "antimicrobial agent" refers to agents which destroy microbes (i.e., bacteria, fungi, viruses and microbial spores) thereby preventing their development and pathogenic action.

The term "antimicrobial cyanoacrylate ester composition" refers to polymerizable compositions comprising monomers and/or reactive oligomers of a cyanoacrylate ester or mixture of such esters and an antimicrobial agent. In a preferred embodiment the antimicrobial cyanoacrylate ester composition further comprises a polymerization inhibitor.

Compositions

This invention relates to methods for closing suturable wounds with antimicrobial cyanoacrylate ester compositions which compositions are described in detail below.

As above, the compositions of this invention comprise a polymerizable cyanoacrylate ester and iodine/polymer complexes. The iodine/polymer complexes are compatible with the cyanoacrylate ester as assessed by the fact that these complexes are dispersible or soluble in the cyanoacrylate ester composition in antimicrobially effective concentrations and when so employed, do not cause premature polymerization of the cyanoacrylate ester and do not prevent effective polymerization of the cyanoacrylate ester when applied to mammalian skin. Moreover, the polymerizable cyanoacrylate ester compositions comprising such complexes form a flexible, durable polymeric film having the complex incorporated therein such that iodine is released from the film in sufficient amounts to provide an antimicrobial property to the film when formed in situ on mammalian skin.

As shown in the examples below, many other conventional antimicrobial agents, when added to the cyanoacrylate ester composition cause polymerization of the cyanoacrylate ester as evidenced by gel formation within 24 hours of such addition or, in the case of elemental iodine, prevent in situ polymerization of the cyanoacrylate ester on mammalian skin. Accordingly, such agents are not compatible with the cyanoacrylate ester compositions.

Antimicrobial cyanoacrylate ester compositions useful in the methods described herein are described by Greff, et al., in U.S. Pat. No. 5,684,042 which patent is incorporated herein by reference in its entirety.

The compositions of this invention are prepared by adding the iodine/polymer complex to the cyanoacrylate ester composition. The iodine/polymer complex is preferably added as the commercially available solid composition rather than as the commercially available aqueous solution insofar as the solution can cause premature polymerization of the cyanoacrylate ester which is apparently due to solvent effects.

Upon addition of the solid iodine/polymer complex to the cyanoacrylate ester composition, the resulting system is thoroughly mixed to obtain a homogeneous suspension.

The amount of iodine/polymer complex added to the cyanoacrylate ester composition is a sufficient amount such that the resulting polymeric film is antimicrobial. Preferably, from about 0.5 to about 30 weight percent of the iodine/polymer complex and more preferably from about 1.0 to 20 weight percent is added to the cyanoacrylate ester composition based on the total weight of the composition. Micronization of PVP-I produces a more dispersible, smoother film with enhanced biocidal activity.

The specific amount of iodine/polymer complex required to effect antimicrobial properties in the resulting polymeric film can be readily measured by conventional in vitro assays measuring zones of microbial growth inhibition around the film. Zones of inhibition of at least 0.5 millimeter and preferably 2 millimeters from the edge of the film when tested in the manner of Example 2 below evidence that the polymeric film is antimicrobial. Assessing the amount of iodine/polymer complex required in the polymeric film to effect such a zone of inhibition is well within the skill of the art.

The composition of the antimicrobial complex and the cyanoacrylate ester can be formulated to a specific viscosity to meet disparate demands for the intended application of the composition. For example, relatively low viscosities are often preferred where application is to be made to a large surface area. This preference results from the fact that these forms are less viscous and, accordingly, will permit more facile large surface area application of a thin film. Contrarily, where application is to be made to a specific position on the skin (e.g., elbow surfaces, knee surfaces and the like), higher viscosity compositions, including those containing thixotropic materials, are preferred to prevent "running" of the compositions to unintended locations.

Accordingly, these compositions have a viscosity of from about 2 to 50,000 centipoise at 20° C. For low viscosity applications, viscosity ranges of from about 2 to 1,500 centipoise at 20° C. are preferred. More preferably, the cyanoacrylate ester employed in the composition is almost entirely in monomeric form and the composition has a viscosity of from about 5 to about 500 centipoise at 20° C.

A thickening agent is optionally employed to increase the viscosity of the composition which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like, with PMMA being preferred. Fumed silica is particularly useful in producing a gel for topical application having a viscosity of from about 1500 to 50,000. Suitable thickening agents for the cyanoacrylate ester compositions described herein also include a polymer of the alkyl cyanoacrylate as disclosed in U.S. Pat. Nos. 3,654,239 and 4,038,345 both of which are incorporated herein by reference in their entirety.

Thickening agents are deemed to be biocompatible if they are soluble or dispersible in the composition and are compatible with the skin as measured by the lack of moderate to severe skin irritation.

The cyanoacrylate ester composition can optionally include a biocompatible plasticizer and, when so employed, such plasticizers are preferably included from about 10 to 30 weight percent and more preferably from about 18 to 25 weight percent based on the weight of the composition absent the antimicrobial agent. Particularly preferred biocompatible plasticizers for use in the compositions described herein are dioctylphthalate and tri-n-butyl acetyl citrate.[3,11]

Additionally, the cyanoacrylate ester compositions described herein preferably include a polymerization inhibitor in an effective amount to inhibit premature polymerization of the composition. In a particularly preferred embodiment, this inhibitor is sulfur dioxide which is employed at from about 50 to 500 ppm based on the total weight of the composition absent the antimicrobial agent. Another preferred inhibitor is 4-methoxyphenol which is employed in an amount effective to inhibit premature polymerization, preferably at from about 100–500 ppm based on the total weight of the composition absent the antimicrobial agent. Still another preferred inhibitor is a mixture of glacial acetic acid and sulfur dioxide which is preferably employed at from about 50 to 500 ppm of sulfur dioxide based on the weight of the composition and from about 50 to 500 ppm of glacial acetic acid based on the weight of the composition each in the absence of the antimicrobial agent.

The cyanoacrylate ester compositions may additionally contain one or more optional additives such as colorants, perfumes, rubber modifiers, modifying agents, etc. In practice, each of these optional additives should be both miscible and compatible with the cyanoacrylate ester composition and the resulting polymer. Compatible additives are those that do not prevent the use of the cyanoacrylate esters in the manner described herein.

In general, colorants are added so that the polymer layer formed on the skin will contain a discrete and discernable color. Perfumes are added to provide a pleasant smell to the composition. Rubber modifiers are added to further enhance the flexibility of the resulting polymer layer. The amount of each of these optional additives employed in the composition is an amount necessary to achieve the desired effect.

Additionally, the cyanoacrylate ester composition can optionally comprise a formaldehyde scavenger compound such as those described by Leung, et al.[9] The use of such scavengers has been suggested as enhancing internal in vivo applications of cyanoacrylate esters.

Still further, it is contemplated that the cyanoacrylate composition can optionally comprise an acrylic monomer that will act as a polymeric plasticizer when it copolymerizes with the cyanoacrylate ester composition.[10]

Methods

In the methods of this invention, the above-described compositions are applied to at least one skin surface of the opposed skin sections of the suturable wound of a mammalian patient (e.g., human patient). The opposed skin sections are contacted with each either before or after application of the cyanoacrylate ester composition. In either case, after application of the cyanoacrylate ester, the wound area is maintained under conditions wherein the cyanoacrylate ester polymerizes to join these skin sections together. In general, a sufficient amount of an antimicrobial cyanoacrylate ester composition is employed to cover the wound and the adjacent the skin surface of at least one of the opposed skin sections of the suturable wound.

Upon contact with skin moisture and tissue protein, the antimicrobial cyanoacrylate ester composition will polymerize or, in the case of compositions utilizing partially polymerized cyanoacrylate esters, will further polymerize, at ambient conditions (skin temperature) over about 10 seconds to 60 seconds to provide a solid polymeric film which joins the skin sections thereby closing the wound.

Generally, the composition provides an antimicrobial polymeric film over the separated skin sections thereby inhibiting infection of the wound while promoting healing.

Preferably, when the cyanoacrylate ester composition is applied to at least one of the opposed skin sections of the suturable wound and, after application, the skin sections are brought into apposition, a second application of the antimicrobial cyanoacrylate composition is made to the closed wound to form an antimicrobial film or coating over the closed wound.

In any event, the antimicrobial film formed over the wound has a thickness of less than about 0.5 millimeter (mm), and more preferably the film has a thickness of less than about 0.3 mm. In a particularly preferred embodiment, the thickness of the polymeric film is from about 0.05 millimeter to about 0.5 millimeter and even more preferably from about 0.05 millimeter to about 0.3 millimeter. Such films are formed by applying at least about 0.02 ml of antimicrobial cyanoacrylate ester composition per square centimeter of skin surface area, more preferably from about 0.02 to about 0.1 ml per square centimeter of skin and still more preferably from about 0.02 to about 0.05 ml of antimicrobial cyanoacrylate ester composition per square centimeter of skin.

Polymeric films of such thicknesses form a physical barrier film over the closed wound which film provides protection for the wound by providing an airtight, waterproof seal around and over the wound. Generally, the polymeric film does not limit dexterity but rather can promote faster wound healing.

In either case, the antimicrobial polymeric film should preferably be maintained in a unbroken manner over the entire wound area. This can be assured by careful application of the antimicrobial cyanoacrylate ester composition onto the skin/wound. Additionally, the optional use of a plasticizer in the antimicrobial composition used to form the coating will facilitate the maintenance of this polymeric film in an unbroken manner. Further amounts of antimicrobial cyanoacrylate ester composition can be applied as needed to maintain an unbroken film over the wound area.

The amount of antimicrobial cyanoacrylate ester composition applied onto at least one skin surface of the opposed skin sections of the suturable wound can be controlled by the amount of composition packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is particularly advantageous because it dispenses the composition in a controlled dropwise manner. Other methods for the controlled dispersement of the antimicrobial cyanoacrylate ester composition are as described above including, by way of example, a conventional spray applicator, a brush or solid paddle applicator, and the like.

Upon application of the antimicrobial cyanoacrylate ester composition, the surface skin moisture, tissue protein, and temperature are sufficient to initiate polymerization of the composition. Thereafter, the skin surface is maintained under suitable conditions to allow polymerization to proceed to formation of a polymeric film.

In general, the particular length of time required for polymerization will vary depending on factors such as the amount of composition applied, the temperature of the skin, the moisture content of the skin, the surface area of the wound, and the like. However, in a preferred embodiment, polymerization is generally complete within about 10 seconds to about 60 seconds while the skin is maintained at ambient conditions. During this period, the person to whom application of the antimicrobial cyanoacrylate ester composition has been made merely allows the composition to form a polymeric film and bond the wound closed while minimizing any action to prevent the skin wound form opening and composition from being dislodged from that portion of the skin where it was applied or to adhere to unintended objects. After the antimicrobial polymeric cyanoacrylate has formed, the polymer strongly adheres to the skin, is flexible and waterproof, thereby protecting the wound area and promoting healing.

In general, the film will adhere to the skin for a period of about 1–4 days after which time it sloughs off. Additional applications can be made as required.

Because the cyanoacrylate polymer film is in contact with the suturable wound, it is contemplated that the antimicrobial cyanoacrylate composition can further comprise medicaments to facilitate wound healing such as growth factors (e.g., epidermal growth factor), anti-scarring agents, and the like. Such medicaments are known in the art including, by way of example only, epidermal growth factor (EGF), platelet derived growth factor (PDGF), transforming growth factors (TGF), keratinocyte growth factor (KGF), fibroblast growth factor (FGF) and the like. Such medicaments are included in the composition in an amount effective for their intended purpose. For example, the amount of growth factor incorporated into the antimicrobial cyanoacrylate composition is dictated by the amount of growth factor released from the polymeric film such that growth of the skin in contact with the film is stimulated. Likewise, the amount of anti-scarring agent incorporated into the antimicrobial cyanoacrylate composition is dictated by the amount of such agent released from the polymeric film such that the level of hypertrophic scarring of the skin is reduced. For example, a corticosteroid such as triamcinolone acetonide may be incorporated into the antimicrobial cyanoacrylate composition to prevent formation of keloids in those patients prone to keloid formation.

It is further contemplated that either the growth factor and/or the anti-scarring agent can be incorporated into a gel type material which, in turn, is incorporated into the cyanoacrylate composition. Upon application to the skin, constituent components of the skin can swell the gel thereby releasing the entrapped medicament.

The following examples illustrate certain embodiments of the invention but is not meant to limit the scope of the claims in any way.

EXAMPLES

In the examples below, all temperatures are in degrees celsius (unless otherwise indicated) and all percents are weight percent (also unless otherwise indicated) except for percent inhibition which is true mathematical percentage. Additionally, the following abbreviations have the following meanings. If an abbreviation is not defined, it has its generally accepted meaning.

CFU=colony forming units conc.=concentration flex.=flexibility dur.=durability ml=milliliters mm=millimeters ppm=parts per million PVP-$_2$=polyvinylpyrrolidone iodine complex SAB-DEX=Sabouraud Dextrose TSA=trypticase soy agar

Example 1

The following example examines the compatibility of different antimicrobial agents in cyanoacrylate ester compositions. In particular, the composition employed monomeric n-butyl cyanoacrylate containing 100 ppm sulfur dioxide and 20 weight percent of dioctyl phthalate absent the antimicrobial agent. In each case, either 5 weight percent, 10 weight percent or 20 weight percent of the antimicrobial agent, based on the total weight of the composition, was added thereto and the properties of the resulting composition measured. The antimicrobial agents tested were elemental iodine, solid polyvinylpyrrolidone iodine, a 30% aqueous solution of polyvinylpyrrolidone iodine, silver nitrate, hexachlorophene, merbromin, tetracycline-HCl, tetracycline hydrate, and erythromycin (each of these antimicrobial agents were obtained from Aldrich Chemical Company, Milwaukee, Wis., USA except for PVP-I$_2$ which was purchased from a commercial vendor).

The evaluation included assessing whether the antimicrobial agent was soluble or suspendable in the composition; whether the resulting composition cured upon contact with skin; whether curing provided for a polymeric film in situ on the skin; whether the polymeric film was flexible and durable. Solubility and suspendability were determined visually. The ability of the resulting composition to cure in situ upon application to skin was measured by applying the cyanoacrylate ester composition onto the upper arm of a male human subject and determining whether polymerization proceeded (up to 5 minutes) and, if so, the time required for polymerization. Film forming capabilities on the skin were assessed by visual evaluation. Durability was assessed by determining whether the film was retained on the skin surface for at least 24 hours and flexibility was measured by the ability of the film to be retained on the skin without cracking or peeling for at least 24 hours. The results of this evaluation are summarized in Table I below:

TABLE I

| Antimicrobial Agent | Conc. | Soluble | Curable | Film Formed | Flex. | Dur. |
|---|---|---|---|---|---|---|
| elemental iodine (I$_2$) | ~20% | partially | No (when tested for 5 minutes) | — | — | — |
| PVP-I$_2$ solid | 10% | no suspension[2] | Yes (30 seconds) | Yes | Yes | Yes |
| PVP-I$_2$ solution | 10% | no, gelled[1] | — | — | — | — |
| Silver nitrate | 5% | no, gelled[1] | — | — | — | — |
| Hexachlorophene | 5% | no, gelled[1] | — | — | — | — |
| Merbromin | 5% | no, gelled[1] | — | — | — | — |
| tetracycline.HCl | 5% | no, gelled[1] | — | — | — | — |
| tetracycline hydrate | 5% | no, gelled[1] | — | — | — | — |
| Erythromycin | 5% | no, gelled[1] | — | — | — | — |

TABLE I-continued

| Antimicrobial Agent | Conc. | Soluble | Curable | Film Formed | Flex. | Dur. |
|---|---|---|---|---|---|---|

[1]gel formation within 24 hours of addition of the antimicrobial agent evidences premature polymerization of the cyanoacrylate ester. In such cases, the antimicrobial agent initiates polymerization.
[2]the mixture is readily resuspended with mild agitation. No gel formed over an 8 week period when stored at room temperature.

The above data demonstrates that of the antimicrobial agents tested, only polyvinylpyrrolidone iodine complex was compatible with the cyanoacrylate ester composition and, of the polyvinylpyrrolidone iodine complexes tested, only the solid form was compatible. Evidently, the solvent in the solution form of polyvinylpyrrolidone iodine complex initiated polymerization of the cyanoacrylate ester. Significantly, the suspension formed by the addition of solid polyvinylpyrrolidone iodine complex was curable in situ on human skin resulting in a flexible and durable polymeric film.

In addition to the above, polyvinylpyrrolidone is a well known biocompatible polymer thereby evidencing that such polymers, when complexed with iodine, are suitable for use in the compositions described herein.

Example 2

The following example was conducted to determine whether sufficient polyvinylpyrrolidone iodine complex was incorporated into the polymeric cyanoacrylate film formed in situ to render this film antimicrobial.

A. Preparation of the Inoculum

Specifically, the surfaces of two TSA plates, 100×15 mm, were inoculated with stock cultures (maintained on TSA slants) with the following microorganisms using a sterile inoculating loop: *Staphylococcus aureus* (ATCC No. 6538) and *Staphylococcus epidennidis* (ATCC No. 12228). The plates were incubated at 30° to 35° C. for 24 hours. The surfaces of two SAB-DEX agar plates were streaked with *Candida albicans* and incubated at 20–25° C. for 48 hours.

The cultures were harvested with sterile saline. Each culture suspension was collected in a sterile container and sufficient sterile saline was added to reduce the microbial count to obtain a working suspension of approximately $1 \times 10^8$ CFU's per ml.

The specific microorganisms recited above were selected for inclusion herein because they are common human skin pathogens (bacteria and fungus).

B. Inoculation of Plates

Each of the three test microorganisms was used to inoculate individual TSA plates by streaking them with sterile cotton tip applicators saturated with the appropriate suspension. The plates were allowed to dry.

C. Inhibition Study

Films of polymerized n-butyl cyanoacrylate comprising 0%, 10%, 15%, 20% or 30% iodine polyvinylpyrrolidone complex were formed on 25 mm glass fiber filter disks and then cut into approximately 11 to 13 mm pieces. The pieces were placed in the center of the appropriate inoculated TSA plates. An untreated filter disk was cut into half, and one-half was placed in the center of the appropriate inoculated TSA plate and the other one-half was place in the center of non-inoculated TSA plates, to serve as a negative control. Two inoculated plates of each microorganism were also used as positive controls without the test article. These plates were then incubated for 3 days at 30° to 35° C. After incubation, the plates were removed and examined for any signs of microbial growth inhibition.

The results of this analysis are set forth in Tables II–IV below. The sample sizes reported are the portion of the sample actually in contact with the agar. The sizes of the zone of inhibition include the diameters of the entire zone including the test article size.

TABLE II

Results for *Staphylococcus aureus*

| SAMPLE: n-butyl cyanoacrylate comprising | SAMPLE SIZE[1] (in mm) | ZONE OF INHIBITION[1] (in mm) |
|---|---|---|
| 0% PVP-$I_2$ | 12 | 12 |
| 10% PVP-$I_2$ | 12 | 15 |
| 15% PVP-$I_2$ | 12.5 | 14 |
| 20% PVP-$I_2$ | 11.5 | 15.5 |
| 30% PVP-$I_2$ | 12.5 | 20 |
| Untreated Filter Disk | 13[2] | 13[2] |
| Negative Control | 13[2] | 13[2] |
| Positive Control | n/a | 0 |

TABLE III

Results for *Staphylococcus epidennis*

| SAMPLE: n-butyl cyanoacrylate comprising | SAMPLE SIZE[1] (in mm) | ZONE OF INHIBITION[1] (in mm) |
|---|---|---|
| 0% PVP-$I_2$ | 12 | 12 |
| 10% PVP-$I_2$ | 12.5 | 15 |
| 15% PVP-$I_2$ | 12 | 15.5 |
| 20% PVP-$I_2$ | 12.5 | 20.5 |
| 30% PVP-$I_2$ | 13 | 27.5 |
| Untreated Filter Disk | 13[2] | 13[2] |
| Negative Control | 13[2] | 13[2] |
| Positive Control | n/a | 0 |

TABLE IV

Results for *Candida albicans*

| SAMPLE: n-butyl cyanoacrylate comprising | SAMPLE SIZE[1] (in mm) | ZONE OF INHIBITION[1] (in mm) |
|---|---|---|
| 0% PVP-$I_2$ | 12 | 12 |
| 10% PVP-$I_2$ | 12.5 | 18.5 |
| 15% PVP-$I_2$ | 12.5 | 23 |
| 20% PVP-$I_2$ | 12.5 | 20.5 |
| 30% PVP-$I_2$ | 13 | 29.5 |
| Untreated Filter Disk | 13[2] | 13[2] |
| Negative Control | 13[2] | 13[2] |
| Positive Control | n/a | 0 |

[1]average of two runs
[2]single run only

The above data demonstrates that the compositions of this invention produce a polymeric cyanoacrylate film which have broad spectrum of antimicrobial activity. Based on these results, it is expected that these compositions would be antimicrobial when formed in situ on mammalian skin surfaces.

Example 3

This examples illustrates how the methods of this invention could be practiced. In this example, an antimicrobial cyanoacrylate ester composition is prepared using n-butyl cyanoacrylate, 200 ppm sulfur dioxide and 15 weight percent of PVP-$I_2$ each based on the total weight of the composition. Optionally, 200 ppm methoxyphenol is added to the composition. A small amount, e.g., 0.5 ml, of the composition is placed into a suitable dispensing device such as a high density polyethylene tube (HDPE) with a dispensing tip.

Specifically, a human adult male (age 44 and weighing 100 kg) is surgically treated to remove an infected appendix. After completion of the surgery, the opposed skin surfaces of the suturable wound used to initiate the surgery are closed as follows. The fascia and subdermal structures are closed with DEXON biodegradable sutures. After washing with sterile saline and drying, the epidermis is closed by gently apposing the skin edges by placing two gloved fingers, each about one inch away from the skin edges, to gently draw the skin sections into apposition. A bead of the antimicrobial cyanoacrylate composition is then applied and spread over the apposed skin sections. The skin sections are held in place for approximately 60 seconds while the composition is allowed to polymerize. A further application of the antimicrobial cyanoacrylate composition is then applied and spread around the wound area to about 1 cm on each side of the incision site to ensure complete sealing.

From the foregoing description, various modifications and changes in the composition and method will occur to those skilled in the art. All such modifications coming within the scope of the appended claims are intended to be included therein.

What is claimed is:

1. A method for closing suturable wounds in a mammalian patient which method comprises:

applying to at least one of the separated skin sections defining the suturable wound a sufficient amount of an antimicrobial polymerizable cyanoacrylate ester composition so as to cover the skin surface;

bringing the separated skin sections defining the suturable wound into apposition; and polymerizing the antimicrobial cyanoacrylate ester composition so as to join the separated skin sections together, wherein the antimicrobial cyanoacrylate ester composition comprises:
(a) a polymerizable cyanoacrylate ester; and
(b) an antimicrobially effective amount of a complex of iodine molecules with a biocompatible polymer.

2. A method for closing suturable wounds in a mammalian patient which method comprises:

bringing the separated skin sections defining the suturable wound into apposition;

applying to the separated skin sections defining the suturable wound a sufficient amount of an antimicrobial polymerizable cyanoacrylate ester composition so as to cover the skin surface; and polymerizing the antimicrobial cyanoacrylate ester composition so as to join the separated skin sections together, wherein the antimicrobial cyanoacrylate ester composition comprises:
(a) a polymerizable cyanoacrylate ester; and
(b) an antimicrobially effective amount of a complex of iodine molecules with a biocompatible polymer.

3. A method according to claim 1 or 2 wherein the polymerizable cyanoacrylate ester is a polymerizable monomer or reactive oligomer of a cyanoacrylate ester which, in monomeric form, is represented by formula I:

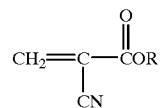

wherein R is selected from the group consisting of:
alkyl of 1 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

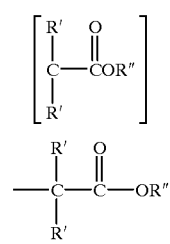

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

4. A method according to claim 3 wherein R is alkyl of from 4 to 10 carbon atoms.

5. A method according to claim 4 wherein R is selected from the group consisting of butyl, pentyl or octyl.

6. A method according to claim 5 wherein R is n-butyl.

7. A method for closing suturable wounds in a mammalian patient which method comprises:

applying to at least one of the separated skin sections defining the suturable wound a sufficient amount of an antimicrobial polymerizable cyanoacrylate ester composition so as to cover the skin surface;

bringing the separated skin sections defining the suturable wound into apposition; and polymerizing the antimicrobial cyanoacrylate ester composition so as to join the separated skin sections together, wherein the antimicrobial cyanoacrylate ester composition comprises:
(a) a polymerizable cyanoacrylate ester; and
(b) an antimicrobially effective amount of a complex of iodine molecules with a biocompatible polymer wherein said complex of iodine molecules with a biocompatible polymer is polyvinylpyrrolidone iodine.

8. A method according to claim 1 wherein, after closure of the suturable wound, further antimicrobial cyanoacrylate composition is applied to the closed wound to form an antimicrobial film or coating over the closed wound.

9. The method according to claim 8 wherein said coating has a thickness of less than about 0.5 millimeter.

10. The method according to claim 2 wherein said cyanoacrylate polymer composition covering the wound has a thickness of less than about 0.5 millimeter.

11. A method according to claim 1 or 2 wherein the antimicrobial cyanoacrylate ester composition further comprises a polymerization inhibitor.

12. A method for closing suturable wounds in a mammalian patient which method comprises:
    applying to at least one of the separated skin sections defining the suturable wound a sufficient amount of an antimicrobial polymerizable cyanoacrylate ester composition so as to cover the skin surface;
    bringing the separated skin sections defining the suturable wound into apposition; and
    polymerizing the antimicrobial cyanoacrylate ester composition so as to join the separated skin sections together,
    wherein the antimicrobial cyanoacrylate ester composition which comprises:
    (a) a polymerizable cyanoacrylate ester which, in monomeric form, is represented by formula II:

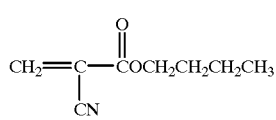

II (b) an antimicrobially effective amount of polyvinylpyrrolidone iodine complex.

13. A method for closing suturable wounds in a mammalian patient which method comprises:
    bringing the separated skin sections defining the suturable wound into apposition;
    applying to the separated skin sections defining the suturable wound a sufficient amount of an antimicrobial polymerizable cyanoacrylate ester composition so as to cover the skin surface; and
    polymerizing the antimicrobial cyanoacrylate ester composition so as to join the separated skin sections together,
    wherein the antimicrobial cyanoacrylate ester composition which comprises:
    (a) a polymerizable cyanoacrylate ester which, in monomeric form, is represented by formula II:

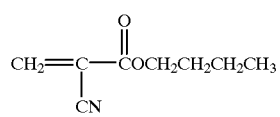

II (b) an antimicrobially effective amount of polyvinylpyrrolidone iodine complex.

14. An antimicrobial cyanoacrylate ester composition which comprises:
    (a) a polymerizable cyanoacrylate ester;
    (b) an antimicrobially effective amount of a complex of iodine molecules with a biocompatible polymer; and
    (c) an effective amount of growth factor to stimulate growth of mammalian skin.

15. An antimicrobial cyanoacrylate ester composition which comprises:
    (a) a polymerizable cyanoacrylate ester;
    (b) an antimicrobially effective amount of a complex of iodine molecules with a biocompatible polymer; and
    (c) an effective amount of an anti-scarring agent to control scarring of mammalian skin at a wound site.

16. The antimicrobial cyanoacrylate ester composition of claim 14 wherein the growth factor is selected from the group consisting of epidermal growth factor, platelet derived growth factor, transforming growth factors, keratinocyte growth factor and fibroblast growth factor.

17. The antimicrobial cyanoacrylate ester composition of claim 15 wherein the anti-scarring agent is triamcinolone acetonide.

* * * * *